United States Patent [19]
Mauvernay et al.

[11] 3,936,450
[45] Feb. 3, 1976

[54] ANTI-INFLAMMATORY AGENTS AND METHOD FOR THEIR PREPARATION

[75] Inventors: Roland Yves Mauvernay, Riom; Norbert Bush, Loubeyrat; Jacques Simond, Chamalieres; Andre Monteil, Gerzat; Jacques Moleyre, Mozac, all of France

[73] Assignee: Centre Europeen de Recherches Mauvernay "C.E.R.M.", Riom, France

[22] Filed: Feb. 7, 1973

[21] Appl. No.: 330,455

[30] Foreign Application Priority Data

Feb. 8, 1972   United Kingdom................ 5827/72

[52] U.S. Cl................. 260/247.7 Z; 260/293.83; 260/326.5 R; 260/570 R; 424/248; 424/267; 424/274; 424/330
[51] Int. Cl.²................ C07D 295/00; C07C 87/29
[58] Field of Search.... 260/247.7 Z, 293.83, 297 R, 260/326.5 C, 326.5 R, 570 R

[56]         References Cited
      FOREIGN PATENTS OR APPLICATIONS
2,000,030   9/1970   Germany......................... 260/247.5
   63,372   8/1968   Germany......................... 260/247.5

Primary Examiner—Lorraine A. Weinberger
Assistant Examiner—Richard D. Kelly
Attorney, Agent, or Firm—Haseltine, Lake & Waters

[57]          ABSTRACT

Tetra-substituted ethylenes having the general formula

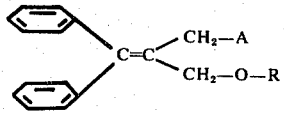

in which R is selected from the group consisting of alkyl radicals containing 1 to 4 carbon atoms and

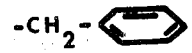

and A is selected from the group consisting of

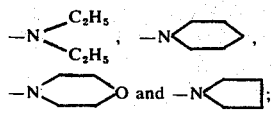

and salts thereof with pharmacologically acceptable acids are useful as anti-inflammatory agents.

7 Claims, No Drawings

ANTI-INFLAMMATORY AGENTS AND METHOD FOR THEIR PREPARATION

This invention relates to tetra-substituted ethylenes to the production thereof and to the use thereof. These uses occur particularly as anti-inflammatory therapeutic agents and, in the case of some of the compounds, also as cardio-vascular therapeutic agents.

The tetra-substituted ethylenes according to the present invention may be represented by the following general formula

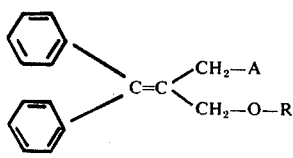
(I)

in which R is an aliphatic, ar - aliphatic or aryl group and A is a tertiary amino group in which the nitrogen atom may be part of a cyclic or heterocyclic group such as pyridine, piperidine, pyrrolidine or morpholine. The invention also includes salts of the said compounds with pharmacologically acceptable acids such as the hydrochlorides and acid fumarates.

Certain compounds having a structure rather similar to those of the present invention have already been described in the literature. Thus A. H. Becket, A. F. Casy, N. J. Harper and P. H. Phillips, J. Pharm. Pharmacol. volume 8, page 860 (1956) have described a substance having the formula:

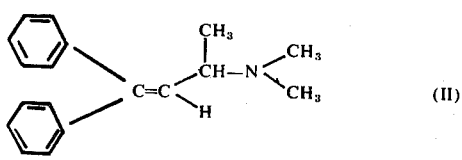
(II)

whilst D. W. Adamson et al, Nature, volume 168, page 204 (1951) have described a substance of the formula:

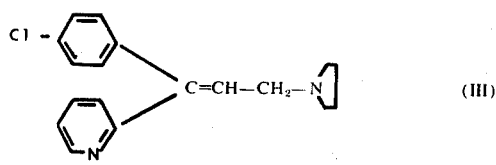
(III)

Each of these two substances possesses the properties of an antihistamine.

In French Pat. No. 1,237,352 we have described a group of substances corresponding to the general formula:

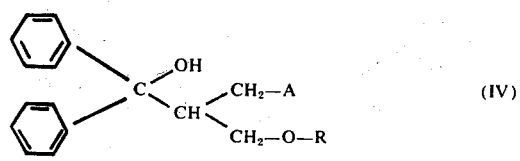
(IV)

in which A and R are as defined above, as well as describing the interesting cardio-vascular properties which these substances possess.

The present invention stems from the discovery that by the dehydration of the compounds having the general formula IV above there are obtained new substances, that is to say the tetra-substituted ethylenes having the general formula I given above which may have an application in human therapeutics in the treatment of inflammation and in some instances in cardio-vascular ailments.

Accordingly one aspect of the invention consists in the provision of compounds having the general formula I.

A second aspect of the invention consists in the provision of a process for the preparation of compounds having the general formula I, this process being characterized by the dehydration of compounds having the general formula IV by means of thionyl chloride.

The compounds having the general formula IV may themselves be obtained from amino-alcohols having the general formula $$R-O-CH_2-CH-CH_2-A$$
$$|$$
$$OH$$

by a process in which the compounds are first treated with a solution of thionyl chloride in chloroform so as to obtain the corresponding chloro compounds and the latter are subsequently condensed with benzophenone dissolved in liquid ammonia. This process for obtaining the starting materials of the formula IV is described in French Pat. No. 1,237,352.

The process for the dehydration of the propanols which form the effective starting materials in the process of the invention utilizes thionyl chloride and involves heating a solution in chloroform or other inert solvent under reflux. This gives the corresponding hydrochlorides from which the bases may be liberated by treatment with an alkali.

The following examples illustrate the invention.

EXAMPLE 1

Preparation of
[1,1-diphenyl-2-ethoxymethyl-2-(pyrrolidine-1)methyl] ethylene as the hydrochloride

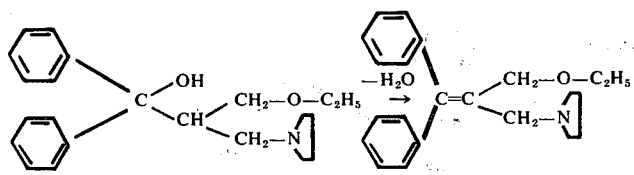

To a solution of 140 gms of N-[2-bisphenylhydroxymethyl)-3-ethoxypropyl] pyrrolidine in 600 ml. of anhydrous chloroform there is gradually added a solution of 300 ml. of thionyl chloride in 300 ml. of chloroform with brisk agitation and whilst maintaining the temperature at or below 45°C. Thereafter the reaction mixture is heated for four hours under reflux, poured onto 200 grams of crushed ice, rendered alkaline with washing soda and extracted with ether. After removal of the ether, the residue is dissolved in 100 ml. of methanol and the product allowed to crystallize. There is thus obtained 66 – 70 grams of the desired product. Melting point 95°C.

The hydrochloride is prepared therefrom by dissolving the product in ethyl acetate and adding thereto a saturated solution of anhydrous hydrogen chloride in absolute ethanol. The hydrochloride has M = 357.9 and a melting point of 160°C.

| Analysis | C% | H% | N% | HCl% |
|---|---|---|---|---|
| Calculated | 73.82 | 7.88 | 3.91 | 10.18 |
| Found | 74.00 | 8.07 | 4.00 | 10.17 |

There are set out in the appended table the names and properties of a number of tetra-substituted ethylenes in accordance with the invention which have been obtained by the above procedure. It will be observed that the compound No. 5 is the one the preparation of which has been described in the preceding example.

TABLE I

| COMPOUND NO. | R | A | SALT/BASE MELTING POINT°C | C CALCULATED | C FOUND | H CALCULATED | H FOUND | N CALCULATED | N FOUND |
|---|---|---|---|---|---|---|---|---|---|
| 1 | —CH$_2$—phenyl | —N(C$_2$H$_5$)$_2$ | Hydrochloride 160° | 76.84 | 76.04 | 7.64 | 7.43 | 3.32 | 3.30 |
| 2 | —CH$_2$—phenyl | piperidine | Fumarate 159° | 74.82 | 74.12 | 6.86 | 7.23 | 2.72 | 2.70 |
| 3 | —CH$_2$—phenyl | morpholine | Fumarate 158° | 72.21 | 72.33 | 6.45 | 6.41 | 2.71 | 2.74 |
| 4 | —CH$_2$—phenyl | pyrrolidine | Fumarate 140° | 74.52 | 74.42 | 6.65 | 7.00 | 2.80 | 2.81 |
| 5 | —CH$_2$—CH$_3$ | pyrrolidine | Hydrochloride 160° | 73.82 | 74.00 | 7.88 | 8.07 | 3.91 | 4.00 |
| 6 | —CH$_2$—CH$_2$—CH$_3$ | pyrrolidine | Hydrochloride 112° | 74.27 | 74.08 | 8.12 | 8.18 | 3.76 | 3.75 |
| 7 | —CH$_2$—CH(CH$_3$)$_2$ | pyrrolidine | Fumarate 175° | 72.25 | 72.55 | 7.52 | 7.63 | 3.01 | 3.01 |
| 8 | —CH$_3$ | morpholine | Base 64° | 77.98 | 77.97 | 7.79 | 8.14 | 4.33 | 4.34 |
| 9 | —CH$_3$ | pyrrolidine | Hydrochloride 177°6 | % Cl Theory 10.61 Found 10.61 | | | | | |
| 10 | —CH$_3$ | —N(C$_2$H$_5$)$_2$ | Hydrochloride 122° | % Cl Theory 10.55 Found 10.57 | | | | | |
| 11 | —C$_2$H$_5$ | piperidine | Hydrochloride 171° | % Cl Theory 9.61 Found 9.78 | | | | | |
| 12 | —C$_2$H$_5$ | morpholine | Hydrochloride 176°5 | % Cl Theory 9.76 Found 9.74 | | | | | |

TABLE I-continued

| COM-POUND NO. | R | A | SALT/BASE MELTING POINT°C | C CALCULATED | C FOUND | H CALCULATED | H FOUND | N CALCULATED | N FOUND |
|---|---|---|---|---|---|---|---|---|---|
| 13 | —CH$_2$—CH$_2$—CH$_3$ | (cyclohexyl-O) | Hydrochloride 154° | 71.20 | 72.59 | 7.79 | 7.86 | 3.61 | 3.67 |
| 14 | —CH$_2$—CH$_2$—CH$_3$ | (cyclohexyl-N) | Hydrochloride 132° | 74.68 | 74.20 | 8.35 | 8.19 | 3.63 | 3.60 |
| 15 | —C$_2$H$_5$ | —N(C$_2$H$_5$)$_2$ | Base 57° | 81.56 | 81.08 | 9.03 | 8.86 | 4.32 | 4.29 |
| 16 | —CH$_2$—CH$_2$—CH$_3$ | —N(C$_2$H$_5$)$_2$ | Base 60° | 81.84 | 80.70 | 9.26 | 9.27 | 4.15 | 4.21 |

The pharmacological activity of the compounds in accordance with the present invention in the cardiovascular and anti-inflammatory fields was ascertained in the following manner.

I. ANTI-INFLAMMATORY ACTIVITY

This was determined on Wistar rats using the induced oedema test employing carraghen. The rats were females weighing 120 ± 20 grams which were first allowed to fast for 18 hours.

The product to be tested was administered to batches of 10 animals at the rate of 100 mg/kg body weight 30 minutes before a subneurotic injection of carraghen to the right rear paw. The odematic reaction is measured hourly for 7 hours by plethysmography, the results being expressed as the "planimetric value" (sum of the % reduction in the increase in volume for the treated groups compared with the control group).

The values obtained under the same conditions using phenyl butazone and hydrocortisone are given for comparison.

| Compound No. | Planimetric Value |
|---|---|
| 1 | 308 |
| 2 | 125 |
| 3 | 80 |
| 4 | 85 |
| 5 | 284 |
| 6 | 267 |
| 8 | 153 |
| 9 | 462 |
| 10 | 402 |
| 11 | 137 |
| 12 | 57 |
| 13 | 344 |
| 14 | 179 |
| 15 | 176 |
| 16 | 130 |
| Phenylbutazone 100 mg/kg B.W. | 237 |
| Hydrocortisone 100 mg/kg B.W. | 230 |

From these results it appears that a reduction in swelling is obtained with all the test products. In particular compounds 1, 5, 6, 9, 10 and 13 show a planimetric value greater than that for the two reference products.

In addition it was considered of interest to make a further study of these six products by employing some more specific tests namely: pleurisy in the rat induced by silver nitrate, subcutaneous granuloma and arthritis induced by the Freund adjuvant.

At the conclusion of these studies, two substances, viz Nos. 5 and 13, demonstrated striking properties compared with other, known, anti-inflammatory substances.

By way of illustration, there are listed below the observations made when carrying out the Freund adjuvant test using the technique described by C. M. Pearson in an article entitled Development of arthritis in the rat following injection with adjuvant-in "Mechanism of Hypersensitivity"— Ed: J. R. Shaffer, G. A. Logrippo and M. W. Chase — Little Brown, Boston 1959, pages 647–671.

The two substances were administered at the rate of 50 mg/kg bodyweight, phenylbutazone used under the same conditions being used as a control.

Observations were made, on the one hand, of the primary swellings (i.e., plethysomographic study of the paw which had been injected) and secondary swellings (i.e., a similar study of the corresponding paw on the opposite side of the body of the animal), and, on the other hand, of the appearance of the bone structures and the joints under X-ray examination.

| SUBSTANCE | SWELLINGS P = primary s=secondary | BONE STRUCTURES AND JOINTS |
|---|---|---|
| Control batch | P : extremely large | -large nodules 'puffing up' of most of the bones |
| | S : delayed, accompanied by anchylosis | |
| | | -hypertrophy of the epiphyses -distinct osteolysis accompanied by disappearance of the bone structure |
| No. 5 | P : not fully reabsorbed | -bone formations and joints not attached |
| | S : completely inhibited | |
| No. 13 | P : not fully reabsorbed | -almost complete protection of the bone structure, some joints only being slightly attacked |
| | S : satisfactory action | |
| Phenylbutazone | P : well reabsorbed | -incomplete protection hypophysary hypartrophies, persistent osteolysis |
| | S : very slight inhibitor. of action | |

In comparison with phenylbatazone, which is a well known anti-inflammatory substance, these compounds have the important advantage that their action extends to the secondary swellings and that they provide complete protection for the bone structure and the joints.

II. CARDIO-VASCULAR ACTIVITY

On account of structural affinities noted in the preamble, the compounds described above were also tested for the above activity on the dog anaesthetized with chloral by measuring the cardiac and haemodynamic parameters in the usual way.

The results obtained, which are expressed below as maximum percentage variations, proved particularly interesting in the case of two substances viz. Nos. 1 and 4.

|  | Compound No. 1 | Compound No. 4 |
|---|---|---|
| Dose administered, in mg/kg (intravenous) | 0.5 | 5 |
| Output of coronary sinus | +49.8 | +81.1 |
| P,O₂ sinusal | +74 | +120.7 |
| Pulse-rate | −11.4 | −29.5 |
| Ventricular inotropism | 0 | −16.5 |
| Arterial pressure | −15.3 | −32.7 |

It may be deduced from an examination of these results that these two compounds have a protective effect on the myocardiam notwithstanding relative hypoxia since the P,O₂ increase cannot be explained merely by the increase in coronary output.

Also to be noted are the fall in pulse-rate and the effectiveness of compound No. 1 at a very small dosage.

The products of the present invention are thus able to be used in human therapeutics, principally for treating acute or chronic rheumatic complaints, and more generally on account of their anti-inflammatory action. Furthermore, certain of these compounds are useful in the treatment of angina and the aftereffects of myocardial infarcation.

These products can be administered in the usual pharmaceutical forms compatible with their physico-chemical properties in doses of from 25 to 200 mg per day, preferably 25 to 100 mg, for the treatment of inflammatory syndromes and 100 to 200 mg for the treatment of cardiac syndromes.

What we claim is:

1. A tetra-substituted ethylene having the general formula

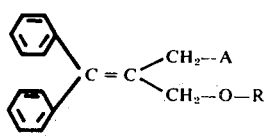

(I)

in which R is selected from the group consisting of alkyl radicals containing 1 to 4 carbon atoms and

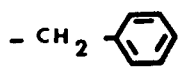

and A is selected from the group consisting of

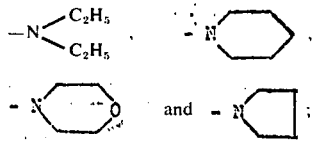

and salts thereof with pharmacologically acceptable acids.

2. A tetra-substituted ethylene according to claim 1 wherein A is

3. A tetra-substituted ethylene according to claim 1 wherein A is

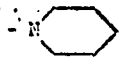

4. A tetra-substituted ethylene according to claim 1 wherein R is

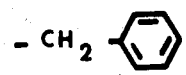

and A is

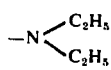

5. A tetra-substituted ethylene according to claim 1 wherein R is

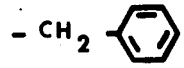

and A is

6. A tetra-substituted ethylene according to claim 1 wherein R is $C_2H_5-$ and A is

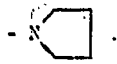

7. A tetra-substituted ethylene according to claim 1 wherein R is $C_3H_7-$ and A is

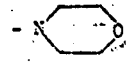

* * * * *